United States Patent [19]

Näf

[11] 4,226,744
[45] Oct. 7, 1980

[54] 5,9-DIMETHYL-DECA-4,9-DIEN-1-AL PERFUME COMPOSITIONS

[75] Inventor: Ferdinand Näf, Geneva, Switzerland

[73] Assignee: Firmenich, S.A., Geneva, Switzerland

[21] Appl. No.: 958,197

[22] Filed: Nov. 6, 1978

[30] Foreign Application Priority Data

Nov. 16, 1977 [CH] Switzerland .................. 13987/77

[51] Int. Cl.² .............................................. C11B 9/00
[52] U.S. Cl. ................................ 252/522 R; 252/89.1; 424/358; 568/485; 568/448
[58] Field of Search ................ 252/522; 260/601 R

[56] References Cited

U.S. PATENT DOCUMENTS 3,493,619   2/1970   Marbet et al. .................. 260/601 R

OTHER PUBLICATIONS

Steffen Arctander, Perfume and Flavor Chemicals, published by author, vol. 1, Monograph 1003, 1969.

*Primary Examiner*—Veronica O'Keefe
*Attorney, Agent, or Firm*—Scully, Scott, Murphy & Presser

[57] ABSTRACT

A novel poly-unsaturated aliphatic aldehyde, viz. 5,9-dimethyl-deca-4,9-dien-1-al, is found to be useful as odor-modifying ingredient. The new aldehyde is particularly useful in the preparation of perfumes and perfumed products.

2 Claims, No Drawings

5,9-DIMETHYL-DECA-4,9-DIEN-1-AL PERFUME COMPOSITIONS

BACKGROUND OF THE INVENTION

I have surprisingly discovered that 5,9-dimethyldeca-4,9-dien-1-al, the aldehyde of formula

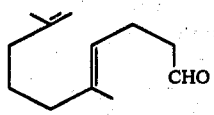
(I)

possesses odorous features of great utility and consequently can be widely utilized in the art of perfumery. Its olfactive character of flowery type is reminiscent of the scent developed by certain plants of the family of liliaceous, more particularly of lily-of-the-valley. Its odour note is "clean," powerful and devoided of fatty tones. This latter aspect is rather surprising since higher aliphatic aldehydes, viz. those aldehydes which possess in the main chain a number of carbon atoms of the order of 8, or higher than 8, develop various odour notes, eminently of fruity type, accompanied however by fatty and waxy notes, especially when used at high concentrations. This fact raises serious problems for perfumers who, in their compounding activity, must often have recourse to complex mixtures in order to mask the unpleasant fatty characters of the aldehydes utilized.

Deca-2,4-dien-1-al for instance develops at low concentration a sweet smell reminiscent of orange. At higher concentration its odour becomes clearly fatty.

Undec-10-en-1-al develops a waxy, rosy odour which for certain of its characters is reminiscent of the odour possessed by citrus fruits. The same odour is presented by undec-2-en-1-al, as well as by decanal and dec-2-en-1-al.

5,9-Dimethyl-deca-4,8-dien-1-al is described as being a compound possessing a sweet, fatty odour with fruity and smoky characters [see U.S. Pat. No. 3,493,619].

The smell of 2,5,9-trimethyl-deca-4,8-dien-1-al has been described as being of "agreably fresh fruity, slightly fatty" type. Finally, in the above mentioned U.S. Patent, 5,9-dimethyl-dec-4-en-1-al is defined as being a compound possessing an odour of "agreably fatty-herbaceous, slightly fruity" type. Concerning their respective odorous properties, the aldehyde of the invention as compared with 5,9-dimethyl-deca-4,8-dien-1-al is characterized by a less aggressive, more pleasant and slightly green character.

Its odour is reminiscent of the flowers of lily-of-the-valley or that of citronellyloxyacetaldehyde giving rise at the same time to a warmer and lighter effect; in contradistinction 5,9-dimethyl-deca-4,8-dien-1-al is more directly reminiscent of dec-9-en-1-al.

THE INVENTION

The present invention is directed to a new composition of matter, viz. 5,9-dimethyl-deca-4,9-dien-1-al.

This invention relates also to a perfume composition which contains a perfuming effective amount of 5,9-dimethyl-deca-4,9-dien-1-al.

The invention provides also a process for enhancing, imparting or modifying the olfactive properties of perfumes and perfumed products which comprises adding thereto a perfuming effective amount of 5,9-dimethyl-deca-4,9-dien-1-al.

Another object of the present invention is a process for enhancing, imparting or modifying the flowery odour characters of perfumes and perfumed products without conferring thereto a fatty note which comprises adding to said perfumes and perfumed products an effective amount of 5,9-dimethyl-deca-4,9-dien-1-al.

Finally this invention relates to a perfumed product comprising as perfuming effective ingredient 5,9-dimethyl-deca-4,9-dien-1-al.

The perfume compositions containing compound (I) can suitably be employed for the compounding of fine perfumes as well as for the perfuming of technical products such as soaps, detergents, house-hold materials or shampoos and cosmetics.

The proportions in which 5,9-dimethyl-deca-4,9-dien-1-al can produce the desired perfuming effects can vary within wide limits. Owing to the absence of fatty notes, which, as we have seen above, is common to the other known higher aliphatic aldehydes, the aldehyde of the invention can be used at high concentrations, in proportions up to 10 or even 20% by weight, based on the total weight of the perfuming composition into which it has been incorporated. Lower concentrations can be of the order of 1 or 2%. The proportions indicated above are not deemed to be interpreted restrictively and values higher or lower than the above given limits can be used whenever special effects are desired, namely in the perfuming of soaps, cosmetics, body deodorizers, air-fresheners or house-hold materials. The determination of the ideal concentration of use depends on the nature of the products into which the critical aldehyde is incorporated and on that of the perfuming coingredients in a given composition. Moreover, subjective factors of consumer's taste and preference in the different market segments are also determinant for making a final assessment as to the best range of concentrations.

5,9-Dimethyl-deca-4,9-dien-1-al is a compound possessing a novel structure. It can be prepared in accordance with methods analogous to prior known ones [see e.g. J. Am. Chem. Soc., 79, 2828 (1957)], for instance starting from isolinalol (3,7-dimethyl-octa-1,7-dien-3-ol) and ethyl-vinyl ether according to the following reaction scheme:

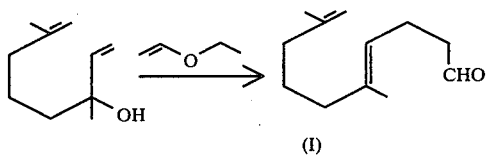
(I)

This is a typical Claisen type reaction which can be effected in the presence of mercury and sodium acetate.

The process followed is illustrated hereinbelow in a more detailed manner.

A mixture of 20 g of isolinalol, 20 g of ethyl-vinyl ether, 6 g of mercury II acetate and 2 g of sodium acetate was heated at 110° C. during 18 h in an autoclave. The reaction mixture was filtered and the clear filtrate was concentrated under reduced pressure, then subjected to a distillation by means of a vessel fitted with a Widmer column. There were thus obtained 8.6 g of a fraction having Bp. 62°–66° C./0.1 Torr constituted by the desired aldehyde (purity about 95%). This product occured as an isomeric trans:cis mixture of weight ratio ca. 2:1. The mixture itself was used as such for the manufacture of perfume compositions or for the perfuming of products as defined by the invention.

NMR(60 MHz): 1.7 (6H); 4.67 (2H); 5.1 (1H, m); 9.7 (1H, s) δppm;

MS: M+ = 180 (1); m/e: 165 (1), 147 (1), 136 (5), 124 (14), 109 (20), 96 (39), 81 (79), 68 (86), 55 (68), 41 (100), 29 (32).

The invention is better illustrated by but not limited to the following examples:

EXAMPLE 1

A base perfume composition of "flowery" type was prepared by mixing the following ingredients together (parts by weight):

|  | Phenylethanol | 300 |
|---|---|---|
|  | Cyclosia base ®* | 200 |
|  | α-Amylcinnamaldehyde | 180 |
|  | p-ter-Butyl-α-methyl-hydroxy-cinnamaldehyde | 120 |
|  | Linalol | 30 |
|  | Dimethylbenzylcarbinol | 60 |
|  | Benzyl salicylate | 20 |
|  | Nerol | 20 |
|  | Farnesol | 10 |
|  |  | 940 |

*Hydroxycitronellal, Firmenich SA, Geneva

By adding to 94 g of the above base, 6 g of 5,9-dimethyl-deca-4,9-dien-1-al there was obtained a novel composition which possessed a characteristic lily-of-the-valley smell.

As a comparison, a novel perfume composition was prepared by admixing to 94 g of the above base 6 g of prior known 5,9-dimethyl-deca-4,8-dien-1-al. The composition thus obtained possessed a flowery-fragrance reminiscent of peony flowers.

EXAMPLE 2

5,9-Dimethyl-deca-4,9-dien-1-al was used to perfume standard articles in the concentrations given below. The stability and the colour of the perfumed articles is indicated in the following scheme:

| Article | Concentration by weight | Temperature [°C.] | Performances stability/colour |
|---|---|---|---|
| Eau-de-toilette | 5% in ethanol | 22 | S/N* |
| Shampoo | 0.2% | 22 | S/N |
| Day beauty cream | 0.4% | 22 | S/N |
| Night beauty cream | 0.4% | 22 | S/N |

*S = stable
N = normal

What I claim is:

1. A perfume composition containing a perfuming effective amount of the compound 5,9-dimethyl-deca-4,9-dien-1-al, said compound imparting a flowery odour character to the perfume composition without conferring thereto a fatty note.

2. Process for enhancing, imparting or modifying the flowery odour characters of perfume compositions without conferring thereto a fatty note which comprises adding to said perfume compositions an effective amount of 5,9-dimethyl-deca-4,9-dien-1-al.